(12) United States Patent
Uhlemann et al.

(10) Patent No.: US 11,454,684 B2
(45) Date of Patent: Sep. 27, 2022

(54) DEVICE AND CONTEXT SPECIFIC SIGNAL PATTERN ANALYSIS FOR MAGNETIC RESONANCE IMAGING EQUIPMENT COMPONENT DIAGNOSTICS AND PREDICTIVE MAINTENANCE

(71) Applicant: KONINKLIJKE PHILIPS N.V., Eindhoven (NL)

(72) Inventors: Falk Uhlemann, Hamburg (DE); Graham Michael Place, Gainesville, FL (US); Ingmar Graesslin, Boenningstedt (DE); Christian Findeklee, Norderstedt (DE); Oliver Lips, Hamburg (DE); Cornelis Jacobus Hendrikus Blom, Lepelstraat (NL)

(73) Assignee: Koninklijke Philips N.V., Eindhoven (NL)

( * ) Notice: Subject to any disclaimer, the term of this patent is extended or adjusted under 35 U.S.C. 154(b) by 594 days.

(21) Appl. No.: 16/490,996

(22) PCT Filed: Mar. 5, 2018

(86) PCT No.: PCT/EP2018/055270
§ 371 (c)(1),
(2) Date: Sep. 4, 2019

(87) PCT Pub. No.: WO2018/162371
PCT Pub. Date: Sep. 13, 2018

(65) Prior Publication Data
US 2020/0011945 A1   Jan. 9, 2020

Related U.S. Application Data

(60) Provisional application No. 62/469,080, filed on Mar. 9, 2017.

(51) Int. Cl.
G06F 11/07 (2006.01)
G01R 33/36 (2006.01)
G01R 33/54 (2006.01)

(52) U.S. Cl.
CPC ............. *G01R 33/36* (2013.01); *G01R 33/54* (2013.01); *G06F 11/079* (2013.01); *G06F 11/0733* (2013.01); *G06F 11/0766* (2013.01)

(58) Field of Classification Search
CPC . G06F 11/0733; G06F 11/0766; G06F 11/079
See application file for complete search history.

(56) References Cited

U.S. PATENT DOCUMENTS

2003/0215125 A1   11/2003   Yokoi et al.
2005/0234330 A1   10/2005   Yokoi et al.
(Continued)

FOREIGN PATENT DOCUMENTS

CN   103376435 A   10/2013
WO   201511556 A1   7/2015

OTHER PUBLICATIONS

International Search Report From PCT/EP2018/055270 dated Jul. 19, 2018.

*Primary Examiner* — Jigar P Patel

(57) ABSTRACT

When predicting required component service in an imaging device such as a magnetic resonance (MR) imaging device (12), component parameters such as coil voltage, phase lock lost (PLL) events, etc. are sampled to monitor system components. Voltage samples are filtered according to their temporal proximity to coil plug-in and unplug events to generate a filtered data set that is analyzed by a processor (46) to determine whether to transmit a fault report. A service recommendation is received based on the transmitted report and includes a root cause diagnosis and service recommendation that is output to a user interface (50).

21 Claims, 7 Drawing Sheets

(56) References Cited

U.S. PATENT DOCUMENTS

| | | |
|---|---|---|
| 2011/0029824 A1 | 12/2011 | Sandoz et al. |
| 2012/0191383 A1 | 7/2012 | Huff et al. |
| 2013/0315349 A1* | 11/2013 | Nguyen ................. H03L 7/091 |
| | | 375/340 |
| 2015/0222278 A1* | 8/2015 | Reichelt ................. H03L 7/102 |
| | | 327/156 |
| 2015/0346717 A1 | 12/2015 | Hosek |

* cited by examiner

DEVICE AND CONTEXT SPECIFIC SIGNAL PATTERN ANALYSIS FOR MAGNETIC RESONANCE IMAGING EQUIPMENT COMPONENT DIAGNOSTICS AND PREDICTIVE MAINTENANCE

CROSS REFERENCE TO RELATED APPLICATIONS

This application is a U.S. national phase application of International Application No. PCT/EP2018/055270 filed on Mar. 5, 2018, which claims the benefit of U.S. Provisional Application Ser. No. 62/469,080 filed on Mar. 9, 2017 and is incorporated herein by reference.

FIELD

The present invention finds application in imaging system maintenance systems and methods. However, it will be appreciated that the described techniques may also find application in other system component fault detection systems, other predictive maintenance techniques, and the like.

BACKGROUND

Detection of device and/or component errors in imaging equipment, such as MR scanners, is a complex task. This task is further impeded by different component versions, e.g., soft- and hardware versions, analogue or digital coils, as well as components from different manufacturers.

In conventional approaches to diagnose a failure or malfunction of imaging equipment, initially a remote service tries to identify the problem via a remote connection to the system. Due to the high uncertainty of this analysis, often multiple field-replaceable-units (FRUs) are sent to the customer site to permit the field service engineer (FSE) to fix the problem. However, this approach results in superfluous components being sent to the customer site. Moreover, failed components often are not correctly identified during the first failure analysis and therefore are not sent, and thus are not on site during the service action. Accordingly, during corrective maintenance, correctly working parts often are needlessly replaced, or working parts together with broken parts are replaced, as the correct identification of a broken coil is usually not trivial. Furthermore, the FSE has to come back on site multiple times to get the imaging equipment fully functional.

The present application provides new and improved systems and methods that facilitate imaging system component failure prediction and root cause determination, thereby overcoming the above-referenced problems and others.

BRIEF SUMMARY

According to a first aspect, a system that facilitates identifying imminent component failure in a magnetic resonance (MR) imaging device based on component signal analysis comprises an MR imaging device comprising a plurality of RF coils, and a connector to which the plurality of coils respectively are connected to a power supply at different times. The system further comprises a processor configured to monitor at least one radio frequency (RF) coil parameter for each of the plurality of RF coils, generate a filtered data set by discarding data points according to at least one predefined metric, and identify at least one fault condition in at least one monitored RF coil based on the filtered data set. The processor is further configured to transmit a report of the identified at least one fault condition, receive a signal comprising information indicative of a root cause of the identified at least one fault condition and a coil service recommendation, and output the coil service recommendation on a user interface (UI).

According to another aspect, a method of identifying imminent component failure in a magnetic resonance (MR) imaging device based on component signal analysis, comprises monitoring at least one radio frequency (RF) coil parameter for each of a plurality of RF coils periodically connected to a power source via a connector, generating a filtered data set by discarding data points collected during monitoring according to at least one predefined metric, and identifying at least one fault condition in at least one monitored RF coil or other subcomponent of the imaging chain based on the filtered data set. The method further comprises transmitting a report of the identified at least one fault condition comprising information indicative of a root cause of the identified at least one fault condition and a coil service recommendation, and outputting the coil service recommendation on a user interface (UI).

According to another aspect, a system that facilitates identifying imminent component failure in a magnetic resonance (MR) imaging device based on component signal analysis, comprises an MR imaging device comprising a plurality of radio frequency (RF) coils, and a connector to which the plurality of coils respectively are connected to a power supply at different times. The system further comprises a processor configured to collect data samples for at least one of phase lock lost (PLL) events and voltage VDL for each of the plurality of RF coils, generate a filtered data set by discarding data samples according to at least one predefined metric, and identify at least one fault condition in at least one monitored RF coil based on the filtered data set. The processor is further configured to transmit a report of the identified at least one fault condition, comprising information indicative of a root cause of the identified at least one fault condition and a coil service recommendation, and making the coil service recommendation available on a user interface (UI).

One advantage is that healthy MR coils are not needlessly replaced.

Another advantage is that failing MR system components are identified prior to actual failure.

Another advantage is that system repair is expedited.

Still further advantages of the subject innovation will be appreciated by those of ordinary skill in the art upon reading and understand the following detailed description.

BRIEF DESCRIPTION OF THE DRAWINGS

The drawings are only for purposes of illustrating various aspects and are not to be construed as limiting.

DETAILED DESCRIPTION

While the following description uses digital RF coils to illustrate the present innovation. The same principle could, of course, be applied to other components for which sufficient diagnostic information is available. The proposed embodiments enable efficient (fast and reliable) and automated remote diagnosis of component (e.g. coil and connectors) faults and broken coils, and thereby mitigate the tedious analysis and skill-level-dependent outcome of complex maintenance tasks. In particular, the present solution facilitates analyzing a wealth of different signals and devices in an automated fashion.

Certain failure modes of components (e.g. a connector problem) exhibit very specific patterns in certain diagnostic signals (e.g. voltages and respective scans) over time. Reference information about the health status of the components (e.g. coils) and their correlation with the respective characteristic time-dependent patterns can be used to diagnose the state or failure of specific components, as well as provide prognostic information. This allows a fine grained root-cause-analysis of potential issues, which cannot be identified using "simple" error thresholds or time-independent correlation such as are found in conventional approaches.

The proposed solution is particularly well-suited for MRI coils due to the complexity of the possible failure modes and the possibility to determine the coil status more efficiently, accurately, and remotely. However, it will be understood by those of skill in the art that the described innovation is applicable to any complex devices and/or components where sufficient prior knowledge and diagnostic information is available.

Figure 1:
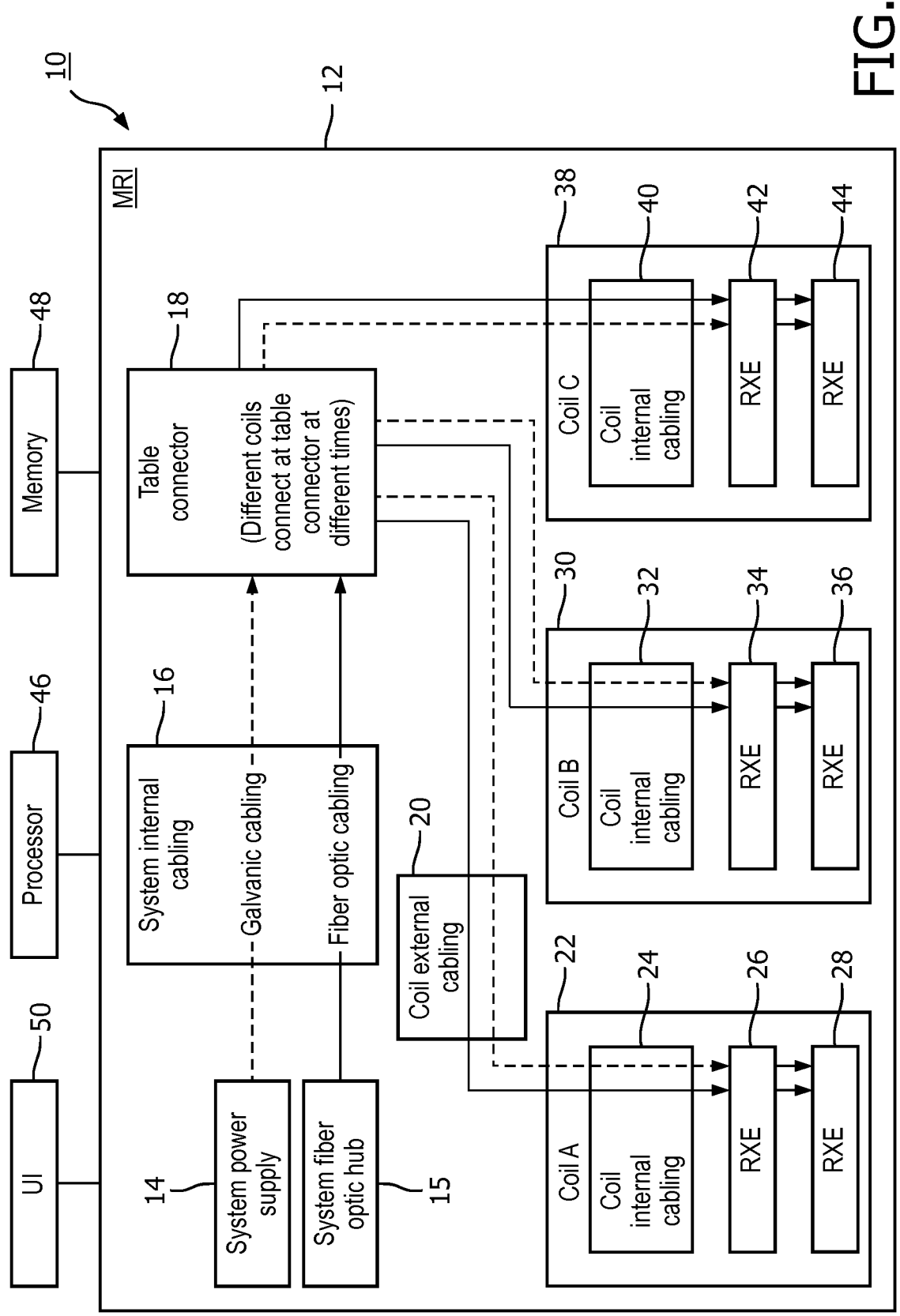
FIG. 1 illustrates a system that facilitates identifying candidate radio frequency (RF) coils for replacement in a magnetic resonance (MR) imaging system, in accordance with one or more aspects described herein.

FIG. 1 illustrates a system 10 that facilitates identifying candidate radio frequency (RF) coils for replacement in a magnetic resonance (MR) imaging system, in accordance with one or more aspects described herein. The system comprises an MR imager 12 having a power supply 14 that provides power via internal cabling 16 (e.g., galvanic cabling for the power supply, or the like) to a connector 18 (e.g., a table connector, a connector located at a magnet in the system, etc.) to which a plurality of RF coils 22, 30, 38 are coupled at different times during one or more MR scans via external cabling 20. Each RF coil 22, 30, 28 comprises respective internal cabling 24, 30, 48 through which power is supplied to a respective first receiver module (RXE) 26, 34, 42 and second receiver module (RXE) 28, 36, 44. The RXE's comprise measurement equipment that logs parameter information (e.g., voltage on a per-second basis if detection is above a threshold). The system 10 also comprises a fiber optic hub 15 that is similarly coupled via internal cabling 16 (e.g., fiber optic cabling or the like for the fiber optic hub) to the connector 18, to which the plurality of RF coils 22, 30, 38 are coupled at different times during one or more MR scans via external cabling 20. Each RF coil 22, 30, 28 comprises respective internal cabling 24, 30, 48 through which signal is supplied to the respective first receiver module (RXE) 26, 34, 42 and second receiver module (RXE) 28, 36, 44.

The MR imaging device 12 is coupled to a processor 46 that executes and a memory 48 that stores computer-executable instructions for performing the various functions, acts, methods, etc. described herein. The memory 48 may be a computer-readable medium on which a control program is stored, such as a disk, hard drive, or the like. Common forms of computer-readable media include, for example, floppy disks, flexible disks, hard disks, magnetic tape, or any other magnetic storage medium, CD-ROM, DVD, or any other optical medium, RAM, ROM, PROM, EPROM, FLASH-EPROM, variants thereof, other memory chip or cartridge, or any other tangible medium from which the processor 46 can read and execute. In this context, the described systems may be implemented on or as one or more general purpose computers, special purpose computer(s), a programmed microprocessor or microcontroller and peripheral integrated circuit elements, an ASIC or other integrated circuit, a digital signal processor, a hardwired electronic or logic circuit such as a discrete element circuit, a programmable logic device such as a PLD, PLA, FPGA, Graphics processing unit (GPU), or PAL, or the like.

Figure 2:
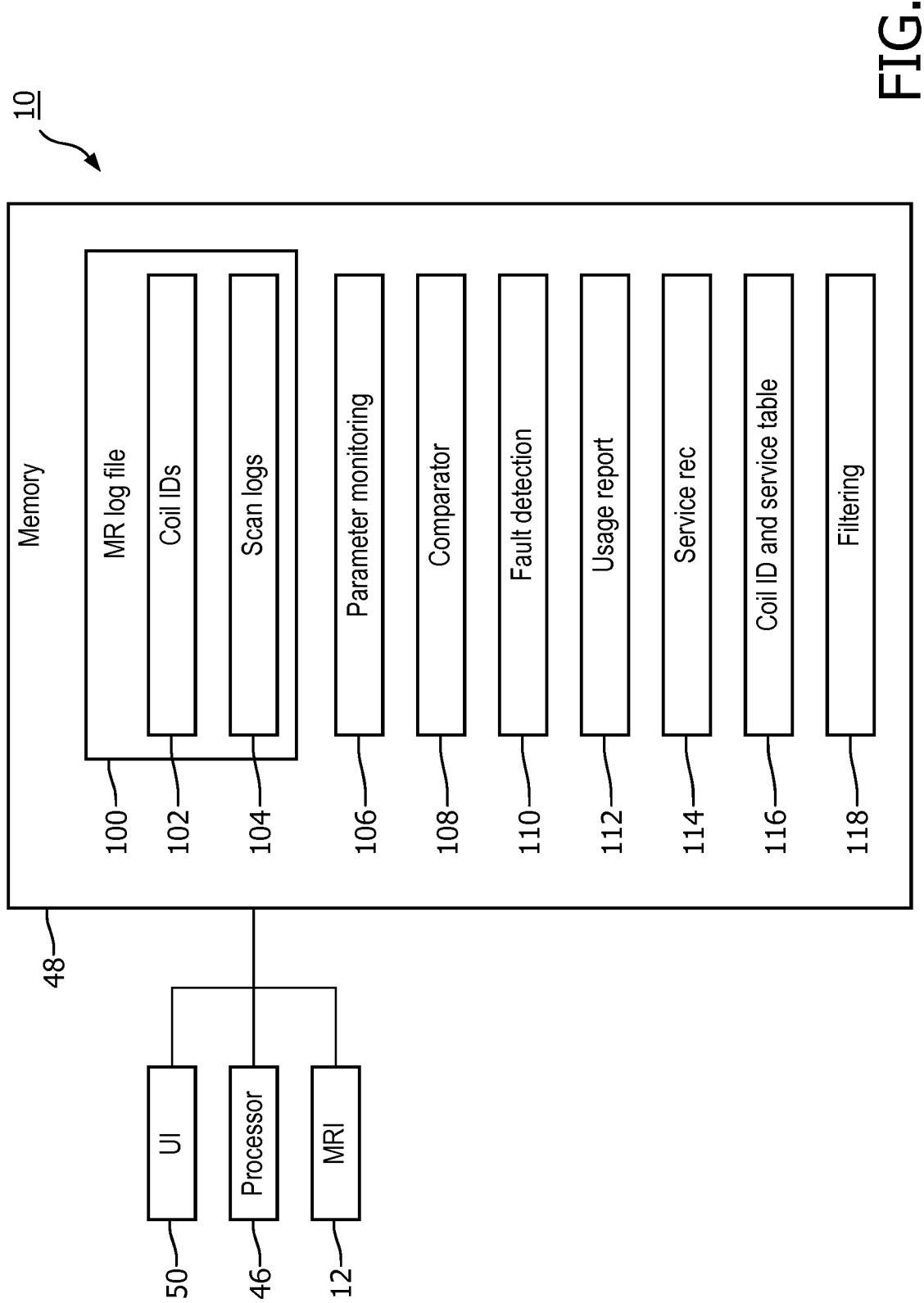
FIG. 2 is an illustration of the system with a more detailed view of components that facilitate performing advance component diagnostics for predictive component replacement, in accordance with various aspects described herein.

FIG. 2 is an illustration of the system 10 with a more detailed view of components that facilitate performing advance component diagnostics for predictive component replacement, in accordance with various aspects described herein. The system includes as stored thereon an MR log file the MR imaging device 12, processor 46, memory 48, and user interface 50. The memory has stored thereon an MR log file 100 that includes coil identification (ID) information 102 for each coil that has been plugged in to MR imaging device via the connector. The log file also includes scan logs 104 that describe the type and duration of scans for which each coil has been used. This information is useful in determining how heavily each coil has been used, which in turn is used to evaluate remaining coil life, etc.

The memory also stores a parameter monitoring module that, when executed by the processor 46, monitors one or more coil parameters. Monitored coil parameters may include, without being limited to: measured voltages; scan type and duration (e.g., head and neck, full-body, contrast scan, etc.); coil age (e.g., since manufacture, installation, etc.); coil version (with it associated failure rate); number of times the coil has used (e.g., how often the connector was used; total scan duration during which the coil was used (total length of use); etc. This monitored parameter information is stored in various log files and storages for analysis by the processor.

The memory further includes a comparator module 108 that, when executed by the processor 46, compares a monitored parameter to a threshold value. Taking measured voltage for example, if the monitored voltage drops below a predetermined threshold, a fault detection module 110 (also executed by the processor) identifies a fault condition in the coil. In another embodiment the fault detection module identifies a fault condition when the measured voltage is below the predetermined threshold for a predetermined number of measurements within a predetermined time period or number of scans. The comparator additionally compares other monitored parameters to other predetermined thresholds. For instance, total use time for a coil can be compared to a predetermined threshold, above which the coil is flagged for imminent failure or preventative replacement, etc.

The processor 46 sends a signal analysis report 112 to a remote server (not shown) periodically (e.g., hourly, daily, etc.) for review. The signal analysis report comprises information related to coil usage, detected fault information, imminent fault information, etc. The processor receives a service recommendation message 114 from the remote server, and presents the service recommendation to an on-site (i.e., at the MR imaging device) technician. The service recommendation presented to the technician may also include recommended actions prior to a final determination that the coil should be replaced. A filtering module 118 is executed by the processor to filter out invalid data points prior to sending data to a remote server for review. The manner in which filtering is performed is described in greater detail with regard to FIG. 6.

Table 1 shows a simplified example of fault information such as is transmitted by the processor 46 for remote diagnostics, (i.e. not at the location of the MR system), based on alerts for systems and respective devices and/or subcomponents created by diagnostic signal analysis.

TABLE 1

| System | Alert | Device | Alert Date | Alert Severity | Status |
|---|---|---|---|---|---|
| Example Hospital New York, USA | RF Coil malfunction | Anterior coil (serial # 1234) | 1.1.2017 | 3 | Being processed |
| General Clinic Berlin, Germany | RF Coil Connector malfunction | Table connector DCC0 | 1.1.2017 | 1 | open |

Table 2 shows an example of a service recommendation report that such as is received by the processor 46. The example instructions are based on alerts created by diagnostic analysis and/or logic for a field service engineer (at the location of the system).

TABLE 2

| Component | Root Cause | Actions |
|---|---|---|
| Anterior coil (serial # 1234) | Electrical contact degradation due to wear | 1. Visual inspection with respect to dust, corrosion or mechanical damage<br>2. Cleaning using brush or spray<br>3. Perform coil connectivity test |
| Table connector DCC0 | Possibly damaged connector pin (voltage V_cc, pin index 3) | 1. Visual inspection with respect to mechanical damage<br>2. Replace connector in case of irreversible damage |

In one embodiment, a service recommendation table 116 is presented on the user interface. The service recommendation table 116 identifies each coil by its coil identification information (e.g., serial number, coil number, or some other suitable identifier) and indicates whether the coil should or should not be replaced. For instance, a coil having a measured voltage that has dropped below the predetermined voltage threshold for a predetermined number of uses or a predetermined number of times within a certain time period is recommended for replacement. Other coils that do not exhibit the low voltage measurements are not recommended for replacement. In another embodiment, the service recommendation table 116 identifies other components of the MR system that require servicing or replacement. For instance, the monitored coil voltage information can be used to determine that a connector that connects one or more of the RF coils to a power source is faulty, and/or that a coil interface that connects one or more of the RF coils to the connector is faulty.

With continued reference to FIGS. 1 and 2, the following figures of various signals over time and descriptions illustrate such a time-dependent characteristic pattern for different signals and how its analysis can be used to distinguish failure-modes and root-causes.

Figure 3:
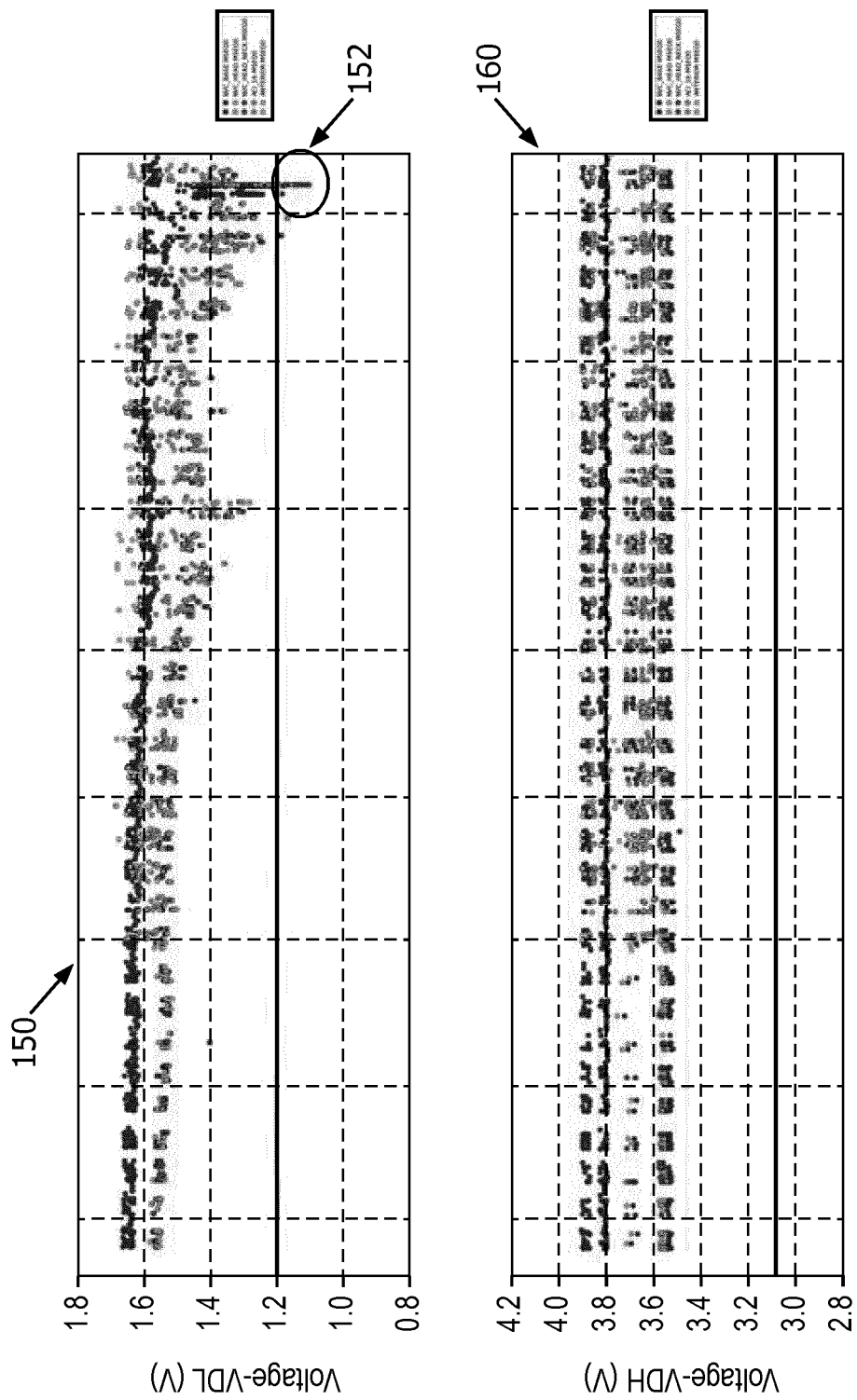
FIG. 3 illustrates graphs of a low voltage (VDL) and a high voltage (VDH) for multiple coils showing progressing degradation of measured voltage levels with a suspected connector issue, in accordance with one or more features described herein.

FIG. 3 illustrates graphs of a low voltage (VDL) 150 and a high voltage (VDH) 160 for multiple coils showing progressing degradation of measured voltage levels with a suspected connector issue, in accordance with one or more features described herein. Measured voltages for each of a plurality of coils is represented by a respective color coded dot. The fluctuation of the voltage indicates an instable or failing state of the internal device network. Employing analysis of the specific involved devices (e.g. coil interface), subsystems (RXEO) and signals (VDL) the failure mode (e.g., a breaking or degrading voltage connection/connector) and the location (e.g. coil interface) can be identified. This kind of signal degradation is used to predict a failure before actual system malfunction, which can be addressed by a respective proactive action.

According to the graph 150, the predetermined voltage threshold is set to 1.2 volts. A coil that is consistently or repeatedly measured below this threshold voltage is considered a candidate for replacement. As can be seen, by the end of the measured time period (e.g., a period of weeks or the like), several coils' voltages have dropped below the 1.2V threshold. In this example, the purple dots denote measured voltages for a head and neck coil. The measured voltages 152 for the head and neck coil (purple) are consistently below the threshold by the end of the monitored time period, and thus the head and neck coil is a candidate for replacement. Other coils, such as the head coil (green), base coil (dark blue) show measured voltages below the threshold, but only sporadically and thus are not recommended for replacement.

Figure 4:
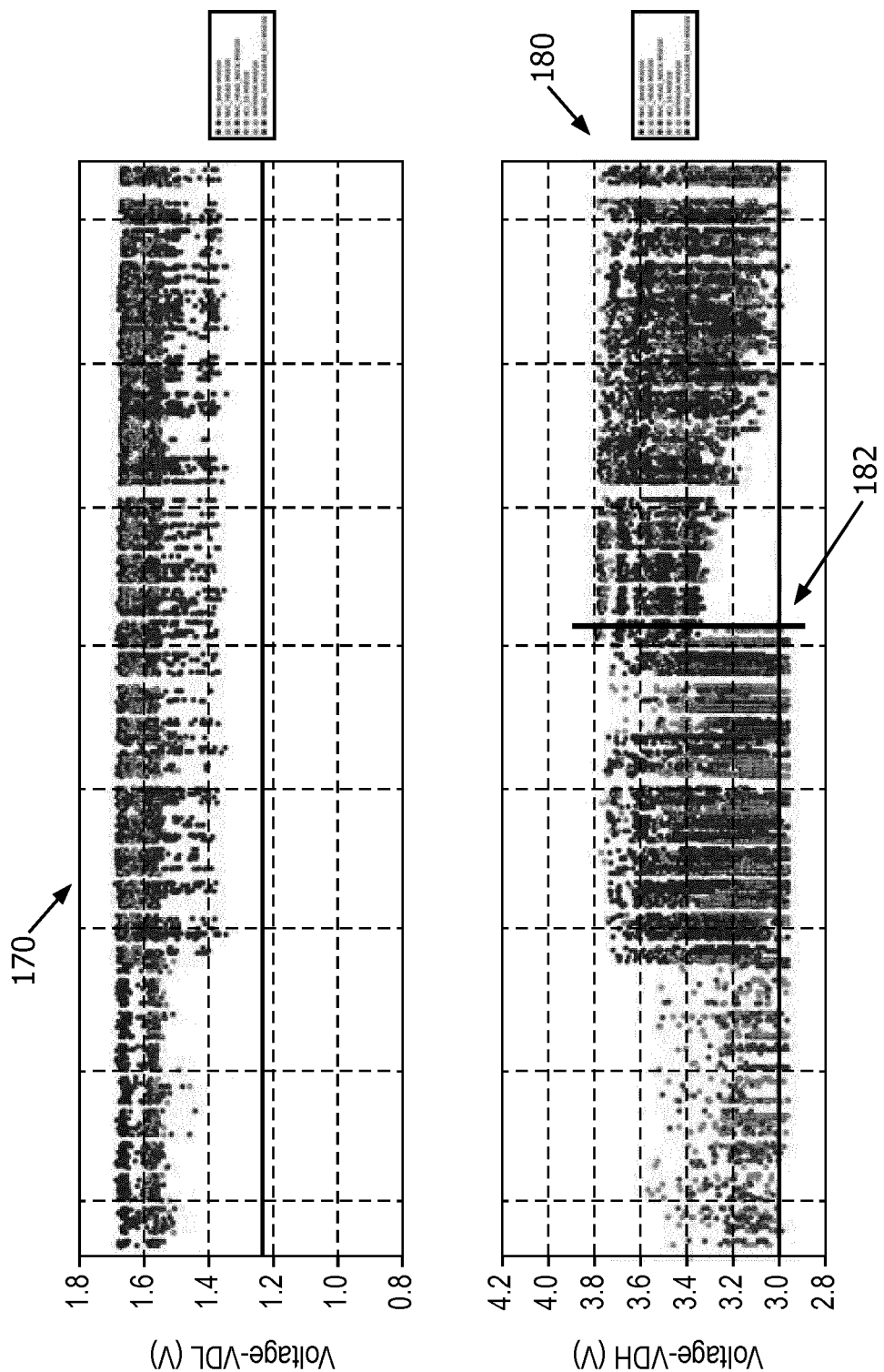
FIG. 4 illustrates graphs of a low voltage (VDL) and a high voltage (VDH) showing a recurring voltage drop, in accordance with one or more features described herein.

FIG. 4 illustrates graphs of a low voltage (VDL) 170 and a high voltage (VDH) 180 showing a recurring voltage drop, in accordance with one or more features described herein. This signal visualization shows a corrective action 182 which has been performed (at about ⅔ of the shown time) after a voltage drop below the specified normal operating range occurred (red line). The action resulted in a normal operating range of the voltage (VDH) for a time.

However, the recurrence of the voltage degradation in VDH shortly after the action indicates, that the root-cause of the failure was not accurately addressed by the initial corrective action. A follow-up action should thus include a broader search for root-causes, especially closer to the power supply, as all coils connected to the system are affected by the voltage issues according to the graphs.

Figure 5:
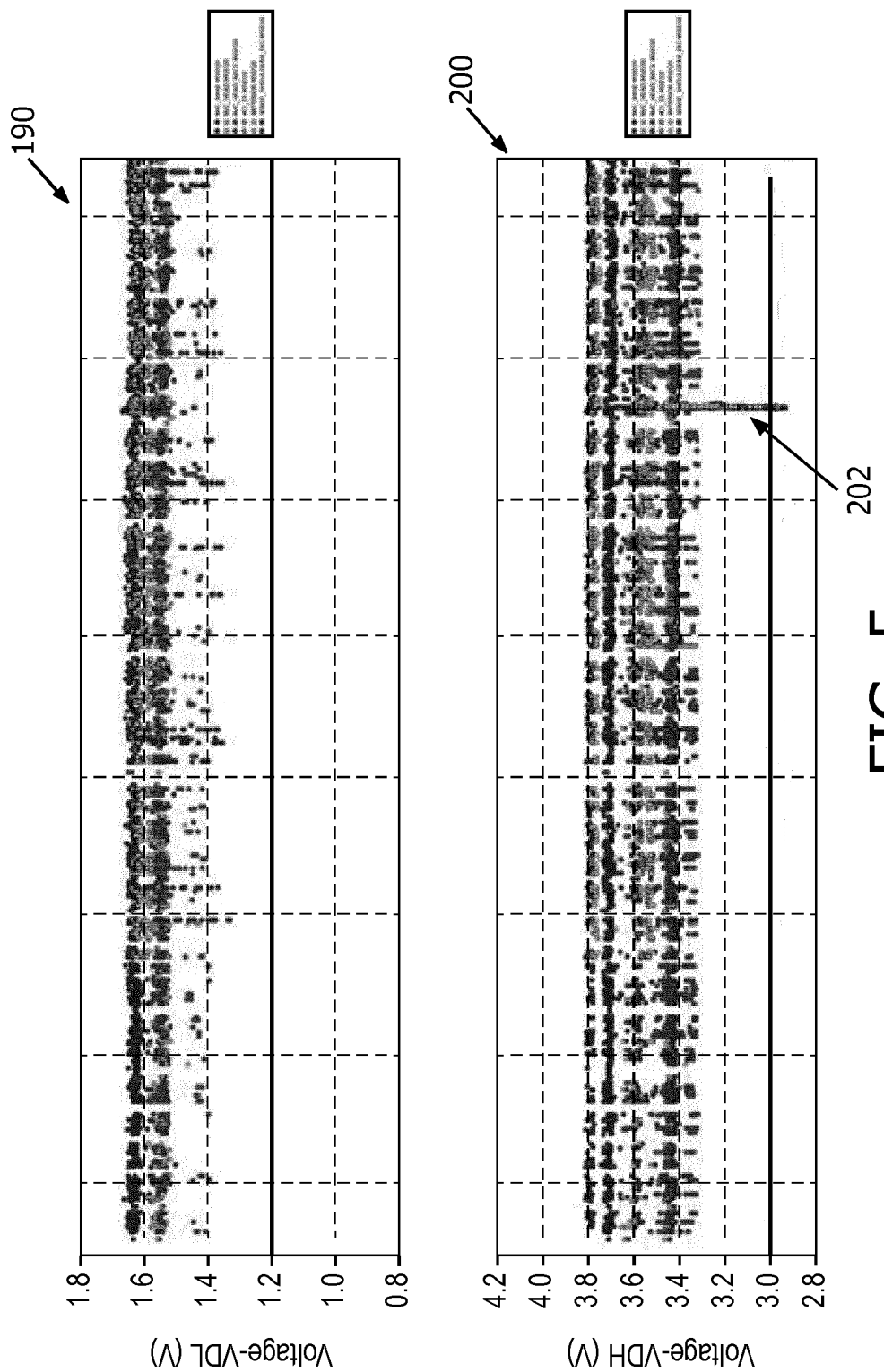
FIG. 5 illustrates graphs of a low voltage (VDL) and a high voltage (VDH) showing short transient voltage issues, in accordance with one or more features described herein.

FIG. 5 illustrates graphs of a low voltage (VDL) 190 and a high voltage (VDH) 200 showing short transient voltage issues, in accordance with one or more features described herein. The signal visualization shows that the signals (VDL, VDH) normally stay above the predetermined threshold (red line). However, at one instance 202 (i.e. during one day at about ¾ of the visualized time) a significant drop of the VDH signal (for all devices) occurs. This indicates that there is not progressing degradation or failing coil/connector issue present but that a transient state of the system lead to a malfunction. This is most probably due to the use/operator of the system and need not incur an immediate corrective action. From the provided examples it is thus clear that the analysis and context of the specific signals and devices provides value information which can be used to identify the failure-mode and/or root-cause of the fault.

The described visual analysis can be performed by appropriate numeric signal analysis, including but not limited to: filtering (windowed or not windowed); correlation; curve-fitting; etc. For instance, out-of-spec events which are do not represent a real malfunction due to their temporal context (i.e. phase lock lost errors during the moment of disconnecting or connecting coils) can be filtered out. In another embodiment, low-pass filtering of signals is performed to eliminate or reduce short transient fluctuations due to the performed scanning. In another embodiment, time-windowed analysis is performed, which ensures only errors present over a specified minimal duration are regarded as errors, to avoid oversensitivity of the signal analysis.

The herein-described MR system has multiple connectors, and multiple coils are connected to each of them. Numerous parameters are monitored by the digital coils, including voltages and other failure modes, such as phase lock lost (PLL). After appropriate filtering of the data, the filtered data from the daily log files is analyzed along with other sources, such as files containing the monitored data (containing data from digital coils, environmental data (technical room and examination room) or other digital components). The connectors may comprise lens systems for transmitting the digitized data as well as supply voltages. After connecting a coil, there is a delay period before all digital internal components provide correct sensor data so that in most cases it is necessary to filter out data around the plug events. Any samples that were logged with a timestamp before the coil was plugged in have to be filtered out, since they represent errors that result from incorrect time synchronization between the coil subsystem and the actual log file. Furthermore, samples that occur immediately after plugging a coil in have to be filtered out, and the duration of the filter constants has to be adapted to the individual parameters being logged. When the second part of two-part coils is plugged in, variations of voltages in the first part (the part already connected) can occur, so that samples logged around plug events of other coils are filtered too. While the delay time at the beginning of monitoring is selected to facilitate filtering (for instance 90 seconds for phase lock lost), the delay time at the end of the scan is selected to be shorter than the time necessary to move the patient out of the imaging device and unplug the coil (e.g., 15 seconds before the unplugged event data samples are filtered out).

Figure 6:
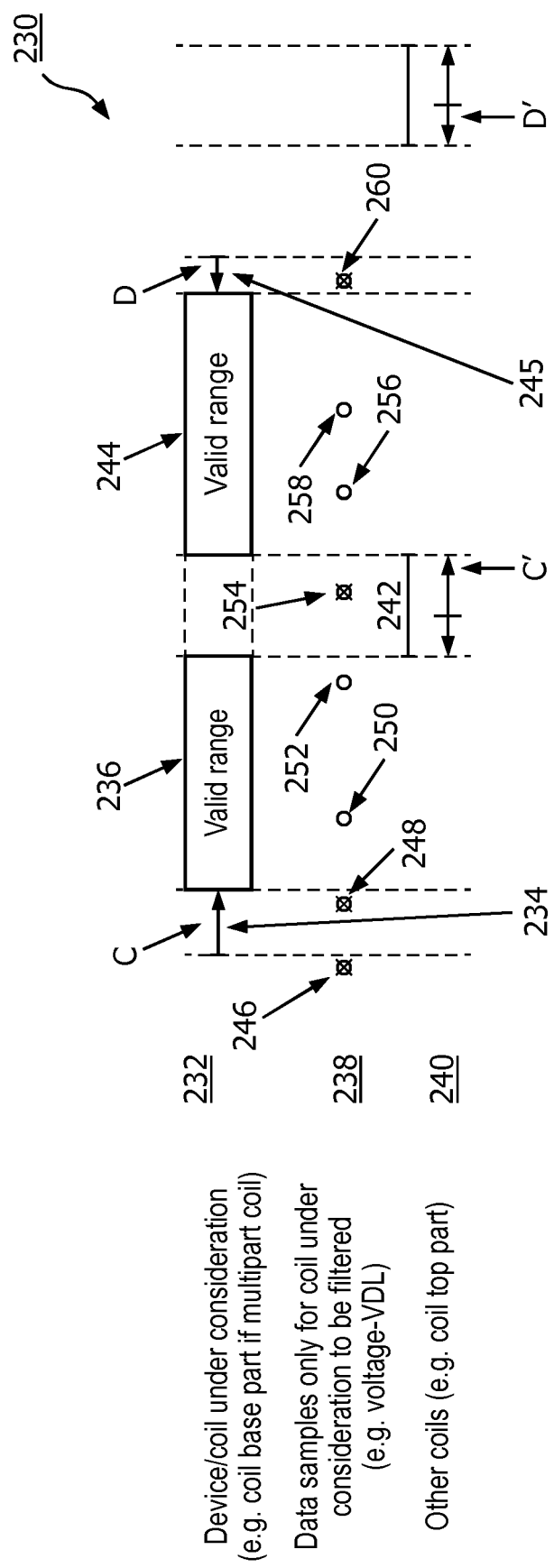
FIG. 6 illustrates a diagram showing a manner in which filtering of measured voltage signals is performed, in accordance with one or more features described herein.

FIG. 6 illustrates a diagram 230 showing a manner in which filtering of measured voltage signals is performed, in accordance with one or more features described herein. Filtering of a signal (indicated by circles for a signal named "voltage VDL" (in the second row) by the processor 46 may be performed in conjunction with a secondary information source which contains information about "plug events" and respective valid measuring ranges, i.e. no signal is considered valid directly after plugging in the coil or directly before unplugging the coil. Consequently, only the circles without red crosses indicate valid data for diagnostic analysis.

In the diagram 230, the top row 232 shows events for a monitored device or coil (e.g., a base coil). The events include a time C at which the base coil is connected, and a time D at which the base coil is disconnected. A connection delay period 234 is illustrated, and spans from the time of connection C to a first valid sampling time period 236. The middle row 238 of the diagram shows data samples collected for a parameter (e.g., voltage VDL) of the monitored coil, wherein the data samples require filtering. The bottom row 240 of the diagram shows events for a different coil (e.g., a top coil) in the system, wherein the events affect the filtering of the data samples for the monitored coil. Specifically, at the time of connection C' of the different coil (e.g., a top coil), voltage VDL of the monitored coil may fluctuate. Therefore, a delay period 242 is shown around the connection time C' during which collected data samples are considered invalid. The different coil is later disconnected at time D'. The After the delay period 242, a second valid sampling range 244 is shown, during which data samples collected for the monitored coil are considered valid. Once the base coil disconnection D is detected, data samples in a delay period 245 spanning from the second valid range 244 until the disconnection D are also considered invalid and filtered out.

In the example of FIG. 6, a data sample 246 is filtered out for occurring prior to the connection of the base coil (i.e., the sample is considered invalid because there should be no voltage VDL prior to connection). A second data sample 248 is filtered out for occurring within the connection delay period (i.e., occurring too soon after the base coil connection to be considered valid). Data samples 250, 252 occur in the first valid sampling range and are therefore not filtered out. Data sample 254 occurs in the delay period 242 between valid sampling ranges 236, 244, during which the top coil was connected, and is therefore filtered out. Data sample 256, 258 occur in the second valid sampling range and are therefore not filtered out. Data sample 260 occur during the disconnection delay period 245 (i.e., too close to the point in time of the base coil disconnection) to be considered valid, and is therefore filtered out. It will be understood that the filtering of invalid data samples is performed by the processor 46 of FIG. 1 by comparing timestamps associated with each data point to the connection and disconnection times of the different coils during a given scan or test procedure, etc.

In one embodiment, when performing filtering, the duration of the plug event delay (the delay period before and after coil plug and unplug events during which data sample points are considered invalid) is selected to so that invalid phase lock lost events are minimized. For instance, if the delay period is too short (e.g., 3 seconds or the like), then false positive PLL events may not be properly filtered out of the data sample set. On the other hand, if the plug event delay period is too long, then actual PLL events may be filtered out unnecessarily.

In another embodiment, QPI (a parameter that is related to spikes that lead to image quality degradation and measured by the MR device) is used to perform filtering of invalid data sets. In order for the sampled parameter data to be comparable between different systems, and in order to create thresholds for all systems, the data need to be normalized, for instance to scan hours or some other suitable metric, and afterwards aggregated on for instance per day basis. According to an example, an upper QPI threshold is set (e.g., 0.5) above which the data sample is considered to represent a fault. If a predetermined number of fault samples of this specific parameter exceeds the threshold, e.g., aggregated on a per day basis, then an alert for service or replacement of the coil can be generated.

In another embodiment, PLL data is aggregated on a per day basis and a sliding window (e.g., having a duration of five days or some other predetermined duration) is used to check whether PLL events have occurred on more than one day within the window. In case more than, e.g., two events fall in sliding window, an alert is generated and sent to a remote server for analysis. The sliding window duration is selected to be long enough that the particular coil being monitored will be connected to the MR imaging device at least two times within the window. For instance, if the MR coil is only used once a week, then a window of 3 weeks, 5 weeks, etc. is selected.

In another embodiment, voltage VDL for each coil is monitored. A predetermined threshold is set below which an alert is generated. It will be understood that the degradation in VDL is monitored across all coils connected to the connector. For instance, if the minimum value of the coil supply voltage (after filtering) falls below the threshold, the data sample is counted as an alert for a coil defect in the case where the low-voltage only occurs for one of multiple coils connected to the connector. However, in the case where multiple coils show the same behavior, then there is a higher probability that the problem is at the connector or power supply for the connector, and the data needs to be analyzed on a per connector basis.

For instance, if the specific coil shows a low voltage on one connector but a normal voltage on a different connector, then the root cause is determined to be a connector issue and not a coil issue. However, in the case wherein only one coil shows a problem at multiple connectors, the root cause is determined to be a defective coil.

Figure 7:
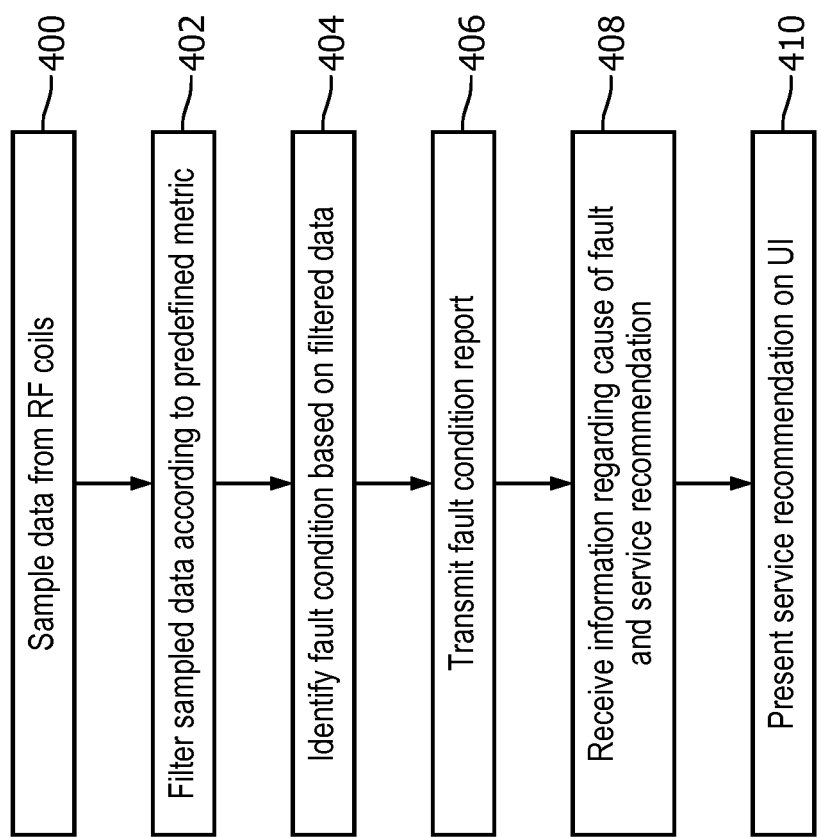
FIG. 7 illustrates a method of identifying imminent component failure in a magnetic resonance (MR) imaging device based on component signal analysis, in accordance with one or more features described herein.

FIG. 7 illustrates a method of identifying imminent component failure in a magnetic resonance (MR) imaging device based on component signal analysis, in accordance with one or more features described herein. At 400, at least one radio frequency (RF) coil parameter is monitored for each of a plurality of RF coils periodically connected to a power source via a connector. At 402, a filtered data set by discarding data points collected during monitoring according to at least one predefined metric. According to one example, when the at least one predefined metric is a plug event delay period that occurs adjacent to and at least one of before and after a given coil is plugged into or unplugged from the connector, the filtered data set can be generated by discarding data samples that fall within a plug event delay period. Additionally or alternatively, when the predefined metric is a predetermined threshold number of PLL events, an alert can be generated when a number of detected PLL events in the filtered data set exceeds the predetermined threshold within a predetermined time period, or a set of time periods determined by filtering for valid time ranges around plug events.

At 404, at least one fault condition in at least one monitored RF coil based on the filtered data set is identified. At 406, a report of the identified at least one fault condition is transmitted to a remote server. At 408, a signal is received from the remote server comprising information indicative of a root cause of the identified at least one fault condition and a coil service recommendation. At 410, the service recommendation is output on a user interface (UI).

The innovation has been described with reference to several embodiments. Modifications and alterations may occur to others upon reading and understanding the preceding detailed description. It is intended that the innovation be construed as including all such modifications and alterations insofar as they come within the scope of the appended claims or the equivalents thereof.

The invention claimed is:

1. A system that facilitates identifying imminent component failure in a magnetic resonance (MR) imaging device based on component signal analysis, comprising:
   an MR imaging device comprising a plurality of radio frequency RF coils;
   a connector to which the plurality of RF coils respectively are connected to a power supply at different times;
   a processor configured to:
      monitor at least one RF coil parameter for each of the plurality of RF coils;
      generate a filtered data set by discarding data points according to at least one predefined metric;
      identify at least one fault condition in at least one system component based on the filtered data set;
      transmit a report of the identified at least one fault condition;
      receive a signal comprising information indicative of a root cause of the identified at least one fault condition and a component service recommendation; and
      output the component service recommendation on a user interface (UI) wherein the at least one monitored parameter is phase lock lost (PLL) events, and wherein the processor is further configured to generate an alert when a number of PLL events exceeds a predetermined threshold within a predetermined time period, or a set of time periods defined by filtering for valid time ranges around plug events.

2. The system according to claim 1, wherein the at least one monitored coil parameter comprises a measured voltage of the at least one RF coil.

3. The system according to claim 2, wherein the processor is further configured to detect a degradation in the measured voltage over time, and wherein the fault condition is identified when the measured voltage is below a predetermined threshold.

4. The system according to claim 1, wherein the component service recommendation output on the UI includes a table identifying each of the plurality of RF coils, and a service recommendation for each RF coil.

5. The system according to claim 4, wherein the table further includes a root cause for a detected fault condition for each RF coil for which service is recommended.

6. The system according to claim 5, wherein the service recommendation is a recommendation to replace the coil when the root cause determined to be a voltage degradation to below a predetermined threshold over a predetermined time period.

7. The system according to claim 1, wherein the RF coils are digital RF coils.

8. The system according to claim 1, wherein the processor is further configured to generate the filtered data set by discarding data points that fall within a plug event delay period.

9. The system according to claim 8, wherein the plug event delay period is a predefined time period that occurs adjacent to and at least one of before and after a given coil is plugged into or unplugged from the connector.

10. The system according to claim 1, wherein the system component is one of:
    a connector that connects one or more of the RF coils to a power source;
    and a coil interface that connects one or more of the RF coils to the connector.

11. A method of identifying imminent component failure in a magnetic resonance (MR) imaging device based on component signal analysis, comprising:

monitoring at least one radio frequency (RF) coil parameter for each of a plurality of RF coils periodically connected to a power source via a connector;
generating a filtered data set by discarding data points collected during monitoring according to at least one predefined metric;
identifying at least one fault condition in at least one system component based on the filtered data set;
transmitting a report of the identified at least one fault condition;
receiving a signal comprising information indicative of a root cause of the identified at least one fault condition and a component service recommendation; and
outputting the component service recommendation on a user interface (UI)
wherein the at least one monitored parameter is phase lock lost (PLL) events, and further comprising generating an alert when a number of PLL events exceeds a predetermined threshold within a predetermined time period, or a set of time periods determined by filtering for valid time ranges around plug events.

12. The method according to claim 11, wherein the at least one monitored coil parameter comprises a periodically measured voltage of the at least one RF coil.

13. The method according to claim 12, further comprising detecting a degradation in the measured voltage over time, and wherein the fault condition is identified when the measured voltage is below a predetermined threshold.

14. The method according to claim 11, wherein the component service recommendation output on the UI includes a table identifying each of the plurality of RF coils, and a service recommendation for each RF coil.

15. The method according to claim 14, wherein the table further includes an identified root cause for a detected fault condition for each RF coil for which service is recommended.

16. The method according to claim 15, wherein the service recommendation is a recommendation to replace the coil when the root cause determined to be a voltage degradation to below a predetermined threshold over a predetermined time period.

17. The method according to claim 11, further comprising generating the filtered data set by discarding data points that fall within a plug event delay period.

18. The method according to claim 17, wherein the plug event delay period is a predefined time period that occurs adjacent to and at least one of before and after a given coil is plugged into or unplugged from the connector.

19. The method according to claim 11, wherein the system component is one of:
a connector that connects one or more of the RF coils to a power source; and
a coil interface that connects one or more of the RF coils to the connector.

20. A system that facilitates identifying imminent component failure in a magnetic resonance (MR) imaging device based on component signal analysis, comprising:
an MR imaging device comprising a plurality of radio frequency (RF) coils;
a connector to which the plurality of coils respectively are connected to a power supply at different times; and
a processor configured to:
collect data samples for at least one of phase lock lost (PLL) events and voltage VDL for each of the plurality of RF coils;
generate a filtered data set by discarding data samples according to at least one predefined metric;
identify at least one fault condition in at least one monitored RF coil based on the filtered data set;
transmit a report of the identified at least one fault condition;
receive a signal comprising:
information indicative of a root cause of the identified at least one fault condition; and
a coil service recommendation; and
output the coil service recommendation on a user interface (UI) (50).

21. The system according to claim 20, wherein the at least one predefined metric is a plug event delay period that occurs adjacent to and at least one of before and after a given coil is plugged into or unplugged from the connector, and wherein the processor is further configured to generate the filtered data set by discarding data samples that fall within a plug event delay period.

* * * * *